(12) United States Patent
Berkenstam et al.

(10) Patent No.: US 7,118,885 B2
(45) Date of Patent: Oct. 10, 2006

(54) NUCLEIC ACID ENCODING VITAMIN D RECEPTOR RELATED POLYPEPTIDE

(75) Inventors: Anders Berkenstam, Stockholm (SE); Mats Dahlberg, Stockholm (SE)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/143,828

(22) Filed: Aug. 31, 1998

(65) Prior Publication Data

US 2003/0032790 A1 Feb. 13, 2003

Related U.S. Application Data

(60) Provisional application No. 60/067,373, filed on Dec. 3, 1997.

(30) Foreign Application Priority Data

Oct. 14, 1997 (SE) .................................... 9703745
Mar. 31, 1998 (SE) .................................... 9801148

(51) Int. Cl.
*C12N 15/11* (2006.01)
*C12N 5/10* (2006.01)
*C12N 15/63* (2006.01)

(52) U.S. Cl. .................. 435/69.1; 435/320.1; 435/325; 536/23.5

(58) Field of Classification Search ............... 435/69.1, 435/320.1, 325; 536/23.4, 23.5
See application file for complete search history.

(56) References Cited

U.S. PATENT DOCUMENTS

| 5,508,164 A | * | 4/1996 | Kausch et al. .................. 435/6 |
| 6,391,847 B1 | | 5/2002 | Evans et al. |
| 6,756,491 B1 | * | 6/2004 | Evans et al. ................ 536/23.1 |
| 6,809,178 B1 | | 10/2004 | Evans et al. |

FOREIGN PATENT DOCUMENTS

| WO | WO8909223 | 10/1989 |
| WO | WO9306215 | 4/1993 |
| WO | WO9317041 | 9/1993 |
| WO | WO9622390 | 7/1996 |
| WO | WO9636230 | 11/1996 |

OTHER PUBLICATIONS

Smith et al, *Nucleic Acids Research*, vol. 22, No. 1 (1994), pp. 66-71.
Blumberg, Bruce et al., "SXR, a novel steroid and xenobiotic-sensing nuclear receptor", *Genes & Development*, 12:3195-3205, 1998.
Fukuen, Shuichi, et al., "Identification of the novel splicing variants for the hPXR in human livers", *Biochemical and Biophysical Research Communications* 298 (2002), 433-438.
Kliewer, Steven A., et al., "An Orphan Nuclear Receptor Activated by Pregnanes Defines a Novel Steroid Signaling Pathway", *Cell*, vol. 92, 73-82, Jan. 9, 1998.
Lehmann, Jürgen M. et al., "The Human Orphan Nuclear Receptor PXR is Activated by Compounds That Regulate CYP3A4 Gene Expression and Cause Drug Interactions", *J. Clin Invest.*, The American Society for Clinical Investigation, Inc., vol. 102, No. 5, Sep. 1998, 1016-1023.
Nuclear Receptors Nomenclature Committee, "A Unified Nomenclature System for the Nuclear Receptor Superfamily", *Cell*, vol. 97, 161-163, Apr. 16, 1999.

* cited by examiner

*Primary Examiner*—Michael Pak
(74) *Attorney, Agent, or Firm*—Gregg C. Benson; Nicholas I. Slepchuk

(57) ABSTRACT

The present invention relates to novel vitamin D receptor related (VDRR) polypeptides, and formulations containing the same. Nucleic acid sequences encoding the VDRR polypeptides, expression vectors containing such sequences and host cells transformed with such expression vectors are also disclosed, as are methods for the expression of the novel VDRR polypeptides of the invention. The invention further relates to VDRR polypeptides for use as medicaments, and use of substances affecting VDRR signal transduction for the manufacture of medicaments for treating metabolic, proliferative or inflammatory conditions. The present invention also relates to methods for identifying clones encoding a VDRR polypeptide, methods for identifying ligands to a VDRR and methods for identifying substances for treatment of conditions affected by a VDRR polypeptide. More specifically, the novel VDRR polypeptide can be the polypeptide designated VDRRγ, which may be regulated by any small chemical molecule similar in structure to known ligands for nuclear receptors.

5 Claims, 15 Drawing Sheets

```
   1 CCTCTGAAGG TTCTAGAATC GATAGTGAAT TCGTGGGACG GGAAGAGGAA
  51 GCACTGCCTT TACTTCAGTG GGAATCTCGG CCTCAGCCTG CAAGCCAAGT
 101 GTTCACAGTG AAAAAAGCAA GAGAATAAGC TAATACTCCT GTCCTGAACA
 151 AGGCAGCGGC TCCTTGGTAA AGCTACTCCT TGATCGATCC TTTGCACCGG
 201 ATTGTTCAAA GTGGACCCCA GGGGAGAAGT CGGAGCAAAG AACTTACCAC
 251 CAAGCAGTCC AAGAGGCCCA GAAGCAAACC TGGAGGTGAG ACCCAAAGAA
 301 AGCTGGAACC ATGCTGACTT TGTACACTGT GAGGACACAG AGTCTGTTCC
 351 TGGAAAGCCC AGTGTCAACG CAGATGAGGA AGTCGGAGGT CCCCAAATCT
 401 GCCGTGTATG TGGGGACAAG GCCACTGGCT ATCACTTCAA TGTCATGACA
 451 TGTGAAGGAT GCAAGGGCTT TTTCAGGAGG CCATGAAAC GCAACGCCCG
 501 GCTGAGGTGC CCCTTCCGGA AGGGCGCCTG CGAGATCACC CGGAAGACCC
 551 GGCGACAGTG CCAGGCCTGC CGCCTGCGCA AGTGCCTGGA GAGCGGCATG
 601 AAGAAGGAGA TGATCATGTC CGACGAGGCC GTGGAGGAGA GGCGGGCCTT
 651 GATCAAGCGG AAGAAAAGTG AACGGACAGG GACTCAGCCA CTGGGAGTGC
 701 AGGGGCTGAC AGAGGAGCAG CGGATGATGA TCAGGGAGCT GATGGACGCT
 751 CAGATGAAAA CCTTTGACAC TACCTTCTCC CATTTCAAGA ATTTCCGGCT
 801 GCCAGGGGTG CTTAGCAGTG GCTGCGAGTT GCCAGAGTCT CTGCAGGCCC
 851 CATCGAGGGA AGAAGCTGCC AAGTGGAGCC AGGTCCGGAA AGATCTGTGC
 901 TCTTTGAAGG TCTCTCTGCA GCTGCGGGGG GAGGATGGCA GTGTCTGGAA
 951 CTACAAACCC CCAGCCGACA GTGGCGGGAA AGAGATCTTC TCCCTGCTGC
1001 CCCACATGGC TGACATGTCA ACCTACATGT TCAAAGGCAT CATCAGCTTT
1051 GCCAAAGTCA TCTCCTACTT CAGGGACTTG CCCATCGAGG ACCAGATCTC
1101 CCTGCTGAAG GGGGCCGCTT TCGAGCTGTG TCAACTGAGA TTCAACACAG
1151 TGTTCAACGC GGAGACTGGA ACCTGGGAGT GTGGCCGGCT GTCCTACTGC
1201 TTGGAAGACA CTGCAGGTGG CTTCCAGCAA CTTCTACTGG AGCCCATGCT
1251 GAAATTCCAC TACATGCTGA AGAAGCTGCA GCTGCATGAG GAGGAGTATG
1301 TGCTGATGCA GGCCATCTCC CTCTTCTCCC CAGACCGCCC AGGTGTGCTG
1351 CAGCACCGCG TGGTGGACCA GCTGCAGGAG CAATTCGCCA TTACTCTGAA
1401 GTCCTACATT GAATGCAATC GGCCCCAGCC TGCTCATAGG TTCTTGTTCC
```

Fig. 1 A

1451 TGAAGATCAT GGCTATGCTC ACCGAGCTCC GCAGCATCAA TGCTCAGCAC
1501 ACCCAGCGGC TGCTGCGCAT CCAGGACATA CACCCCTTTG CTACGCCCCT
1551 CATGCAGGAG TTGTTCGGCA TCACAGGTAG CTGAGCGGCT GCCCTTGGGT
1601 GACACCTCCG AGAGGCAGCC AGACCCAGAG CCCTCTGAGC CGCCACTCCC
1651 GGGCCAAGAC AGATGGACAC TGCCAAGAGC CGACAATGCC CTGCTGGCCT
1701 GTCTCCCTAG GGAATTCCTG CTATGACAGC TGGCTAGCAT TCCTCAGGAA
1751 GGACATGGGT GCCCCCCACC CCCAGTTCAG TCTGTAGGGA GTGAAGCCAC
1801 AGACTCTTAC GTGGAGAGTG CACTGACCTG TAGGTCAGGA CCATCAGAGA
1851 GGCAAGGTTG CCCTTTCCTT TTAAAAGGCC CTGTGGTCTG GGGAGAAATC
1901 CCTCAGATCC CACTAAAGTG TCAAGGTGTG GAAGGGACCA AGCGACCAAG
1951 GATAGGCCAT CTGGGGTCTA TGCCCACATA CCCACGTTTG TTCGCTTCCT
2001 GAGTCTTTTC ATTGCTACCT CTAATAGTCC TGTCTCCCAC TTCCCACTCG
2051 TTCCCCTCCT CTTCCGAGCT GCTTTGTGGG CTCAAGGCCT GTACTCATCG
2101 GCAGGTGCAT GAGTATCTGT GGGAGTCCTC TAGAGAGATG AGAAGCCAGG
2151 AGGCCTGCAC CAAATGTCAG AAGCTTGGCA TGACCTCATT CCGGCCACAT
2201 CATTCTGTGT CTCTGCATCC ATTTGAACAC ATTATTAAGC ACTGATAATA
2251 GGTAGCCTGC TGTGGGGTAT ACAGCATTGA CTCAGATATA GATCCTGAGC
2301 TCACAGAGTT TATAGTTAAA AAAACAAACA GAAACACAAA CAATTTGGAT
2351 CAAAAGGAGA AAATGATAAG TGACAAAAGC AGCACAAGGA ATTTCCCTGT
2401 GTGGATGCTG AGCTGTGATG GCAGGCACTG GGTACCCAAG TGAAGGTTCC
2451 CGAGGACATG AGTCTGTAGG AGCAAGGGCA CAAACTGCAG CTGTGAGTGC
2501 GTGTGTGTGA TTTGGTGTAG GTAGGTCTGT TTGCCACTTG ATGGGGCCTG
2551 GGTTTGTTCC TGGGGCTGGA ATGCTGGGTA TGCTCTGTGA CAAGGCTACG
2601 CTGACAATCA GTTAAACACA CCGGAGAAGA ACCATTTACA TGCACCTTAT
2651 ATTTCTGTGT ACACATCTAT TCTCAAAGCT AAAGGGTATG AAAGTGCCTG
2701 CCTTGTTTAT AGCCACTTGT GAGTAAAAAT TTTTTTGCAT TTTCACAAAT
2751 TATACTTTAT ATAAGGCATT CCACACCTAA GAACTAGTTT TGGGAAATGT
2801 AGCCCTGGGT TTAATGTCAA ATCAAGGCAA AAGGAATTAA ATAATGTACT
2851 TTTGGCTAAA AAAAAAAAAA AAAAAAAAAA AAAAAAAAAA AAAAAAAAAA
2901 AAAAA

Fig. 1 B

```
  1 MEVRPKESWN HADFVHCEDT ESVPGKPSVN ADEEVGGPQI CRVCGDKATG

51 YHFNVMTCEG CKGFFRRAMK RNARLRCPFR KGACEITRKT RRQCQACRLR

101 KCLESGMKKE MIMSDEAVEE RRALIKRKKS ERTGTQPLGV QGLTEEQRMM

151 IRELMDAQMK TFDTTFSHFK NFRLPGVLSS GCELPESLQA PSREEAAKWS

201 QVRKDLCSLK VSLQLRGEDG SVWNYKPPAD SGGKEIFSLL PHMADMSTYM

251 FKGIISFAKV ISYFRDLPIE DQISLLKGAA FELCQLRFNT VFNAETGTWE

301 CGRLSYCLED TAGGFQQLLL EPMLKFHYML KKLQLHEEEY VLMQAISLFS

351 PDRPGVLQHR VVDQLQEQFA ITLKSYIECN RPQPAHRFLF LKIMAMLTEL

401 RSINAQHTQR LLRIQDIHPF ATPLMQELFG ITGS
```

Fig. 4

```
TGAATTCGTGGGCCTGCTGGGTTAGTGCTGGCAGCCCCC    40
TGAGGCCAAGGACAGCAGCATGACAGTCACCAGGACTCAC   80
CACTTCAAGGAGGGGTCCCTCAGAGCACCTGCCATACCCC   120
TGCACAGTGCTGCGGCTGAGTTGGCTTCAAACCATCCAAG   160
AGGCCCAGAAGCAAACCTGGAGGTGAGACCCAAAGAAAGC   200
TGGAACCATGCTGACTTTGTACACTGTGAGGACACAGAGT   240
CTGTTCCTGGAAAGCCCAGTGTCAACGCAGATGAGGAAGT   280
CGGAGGTCCCCAAATCTGCCGTGTATGTGGGACAAGGCC    320
ACTGGCTATCACTTCAATGTCATGACATGTGAAGGATGCA   360
AGGGCTTTTTCAGGAGGGCCATGAAACGCAACGCCCGGCT   400
GAGGTGCCCCTTCCGGAAGGGCGCCTGCGAGATCACCCGG   440
AAGACCCGGCGACAGTGCCAGGCTGCCGCCTGCGCAAGT    480
GCCTGGAGAGCGGCATGAAGAAGGAGATGATCATGTCCGA   520
CGAGGCCGTGGAGGAGAGGCGGGCCTTGATCAAGCGGAAG   560
AAAAGTGAACGGACAGGGACTCAGCCACTGGGAGTGCAGG   600
GGCTGACAGAGGAGCAGCGGATGATGATCAGGGAGCTGAT   640
GGACGCTCAGATGAAAACCTTTGACACTACCTTCTCCCAT   680
TTCAAGAATTTCCGGCTGCCAGGGGTGCTTAGCAGTGGCT   720
GCGAGTTGCCAGAGTCTCTGCAGGCCCCATCGAGGGAAGA   760
AGCTGCCAAGTGGAGCCAGGTCCGGAAAGATCTGTGCTCT   800
TGAAGGTCTCTCTGCAGCTGCGGGGGGAGGATGGCAGTG    840
TCTGGAACTACAAACCCCCAGCCGACAGTGGCGGGAAAGA   880
GATCTTCTCCCTGCTGCCCCACATGGCTGACATGTCAACC   920
TACATGTTCAAAGGCATCATCAGCTTTGCCAAAGTCATCT   960
CCTACTTCAGGGACTTGCCCATCGAGGACCAGATCTCCCT   1000
GCTGAAGGGGGCCGCTTTCGAGCTGTGTCAACTGAGATTC   1040
AACACAGTGTTCAACGCGGAGACTGGAACCTGGGAGTGTG   1080
GCCGGCTGTCCTACTGCTTGGAAGACACTGCAGGTGGCTT   1120
CCAGCAACTTCTACTGGAGCCCATGCTGAAATTCCACTAC   1160
ATGCTGAAGAAGCTGCAGCTGCATGAGGAGGAGTATGTGC   1200
TGATGCAGGCCATCTCCCTCTTCTCCCCAGACCGCCCAGG   1240
TGTGCTGCAGCACCGCGTGGTGGACCAGCTGCAGGAGCAA   1280
TTCGCCATTACTCTGAAGTCCTACATTGAATGCAATCGGC   1320
CCCAGCCTGCTCATAGGTTCTTGTTCCTGAAGATCATGGC   1360
TATGCTCACCGAGCTCCGCAGCATCAATGCTCAGCACACC   1400
CAGCGGCTGCTGCGCATCCAGGACATACACCCCTTTGCTA   1440
```

Fig. 7 A

```
CGCCCCTCATGCAGGAGTTGTTCGGCATCACAGGTAGCTG 1480
AGCGGCTGCCCTTGGGTGACACCTCCGAGAGGCAGCCAGA 1520
CCCAGAGCCCTCTGAGCCGCCACTCCGGGCCAAGACAGA  1560
TGGACACTGCCAAGAGCCGACAATGCCCTGCTGGCCTGTC 1600
TCCCTAGGGAATTCCTGCTATGACAGCTGGCTAGCATTCC 1640
TCAGGAAGGACATGGGTGCCCCCCACCCCAGTTCAGTCT  1680
GTAGGGAGTGAAGCCACAGACTCTTACGTGGAGAGTGCAC 1720
TGACCTGTAGGTCAGGACCATCAGAGAGGCAAGGTTGCCC 1760
TTTCCTTTTAAAAGGCCCTGTGGTCTGGGGAGAAATCCCT 1800
CAGATCCCACTAAAGTGTCAAGGTGTGGAAGGGACCAAGC 1840
GACCAAGGATAGCCATCTGGGGTCTATGCCCACATACCC  1880
ACGTTTGTTCGCTTCCTGAGTCTTTTCATTGCTACCTCTA 1920
ATAGTCCTGTCTCCCACTTCCCACTCGTTCCCCTCCTCTT 1960
CCGAGCTGCTTTGTGGGCTCAAGGCCTGTACTCATCGGCA 2000
GGTGCATGAGTATCTGTGGGAGTCCTCTAGAGAGATGAGA 2040
AGCCAGGAGGCCTGCACCAAATGTCAGAAGCTTGGCATGA 2080
CCTCATTCCGGCCACATCATTCTGTGTCTCTGCATCCATT 2120
TGAACACATTATTAAGCACTGATAATAGGTAGCCTGCTGT 2160
GGGGTATACAGCATTGACTCAGATATAGATCCTGAGCTCA 2200
CAGAGTTTATAGTTAAAAAACAAACAGAAACACAAACAA  2240
TTTGGATCAAAAGGAGAAAATGATAAGTGACAAAAGCAGC 2280
ACAAGGAATTTCCCTGTGTGGATGCTGAGCTGTGATGGCA 2320
GGCACTGGGTACCCAAGTGAAGGTTCCCGAGGACATGAGT 2360
CTGTAGGAGCAAGGGCACAAACTGCAGCTGTGAGTGCGTG 2400
TGTGTGATTTGGTGTAGGTAGGTCTGTTTGCCACTTGATG 2440
GGGCCTGGGTTTGTTCCTGGGCTGGAATGCTGGGTATGC  2480
TCTGTGACAAGGCTACGCTGACAATCAGTTAAACACACCG 2520
GAGAAGAACCATTTACATGCACCTTATATTTCTGTGTACA 2560
CATCTATTCTCAAAGCTAAAGGGTATGAAAGTGCCTGCCT 2600
TGTTTATAGCCACTTGTGAGTAAAAATTTTTTTGCATTTT 2640
CACAAATTATACTTTATATAAGGCATTCCACACCTAAGAA 2680
CTAGTTTTGGAAATGTAGCCCTGGGTTTAATGTCAAATC  2720
AAGGCAAAAGGAATTAAATAATGTACTTTTGGCTAAAAAA 2760
AAAAAAAAAAAAAAAAAAAAAAAAAAAAAAAAAAAAAAAA 2800
AA                                       2802
```

Fig. 7 B

```
MTVTRTHHFKEGSLRAPAIPLHSAAAELASNHPRGPEANL  40
EVRPKESWNHADFVHCEDTESVPGKPSVNADEEVGGPQIC  80
RVCGDKATGYHFNVMTCEGCKGFFRRAMKRNARLRCPFRK 120
GACEITRKTRRQCQACRLRKCLESGMKKEMIMSDEAVEER 160
RALIKRKKSERTGTQPLGVQGLTEEQRMMIRELMDAQMKT 200
FDTTFSHFKNFRLPGVLSSGCELPESLQAPSREEAAKWSQ 240
VRKDLCSLKVSLQLRGEDGSVWNYKPPADSGGKEIFSLLP 280
HMADMSTYMFKGIISFAKVISYFRDLPIEDQISLLKGAAF 320
ELCQLRFNTVFNAETGTWECGRLSYCLEDTAGGFQQLLLE 360
PMLKFHYMLKKLQLHEEEYVLMQAISLFSPDRPGVLQHRV 400
VDQLQEQFAITLKSYIECNRPQPAHRFLFLKIMAMLTELR 440
SINAQHTQRLLRIQDIHPFATPLMQELFGITGS.       474
```

NUCLEIC ACID ENCODING VITAMIN D RECEPTOR RELATED POLYPEPTIDE

CROSS REFERENCE TO RELATED APPLICATIONS

This application claims priority from Swedish Patent Application No. 9703745-1, filed Oct. 14, 1997, Swedish Patent Application No. 9801148-9, filed Mar. 31, 1998. and U.S. Provisional Patent Application Ser. No. 60/067,373, filed Dec. 3, 1997. These applications are incorporated herein by reference in their entirety.

FIELD OF THE INVENTION

The present invention relates to novel vitamin D receptor related (VDRR) polypeptides. Nucleic acid sequences encoding the same, expression vectors containing such sequences and host cells transformed with such expression vectors are also disclosed, as are methods for the expression of the novel VDRR polypeptides of the invention, and uses thereof.

BACKGROUND OF THE INVENTION

Nuclear hormone receptors is a large group of conditionally regulated transcription factors. These receptors are activated and regulate target gene expression in response to binding a variety of small chemical molecules (ligands) including steroids, vitamin D3, retinoids, eicosanoides (prostanoids), thyroid hormone and cholesterol derivatives.

A growing number of structurally related receptors have been identified for which no ligands yet have been identified. This group of receptors is referred to as orphan nuclear receptors (ONRs). A review of the ONRs can be found in Enmark et al, Mol. Endo., vol. 10, No. 11 (1996) pp. 1293–1307, which is hereby incorporated by reference. The pivotal importance of a number of ONRs for processes such as metabolic homeostasis, cell differentiation and development have been demonstrated both by biochemical and genetic techniques. In addition, several ONRs have also been implicated as key factors in a variety of common diseases and disorders such as diabetes, obesity, inflammatory conditions and proliferative diseases.

Based on these findings it is generally believed that novel ONRs are going to become potential drug targets for therapeutic invention of common diseases Thus, it is of great importance to identify such receptors.

SUMMARY OF THE INVENTION

The present invention relates to novel vitamin D receptor related (VDRR) polypeptides, and formulations containing the same. Nucleic acid sequences encoding the VDRR polypeptides, expression vectors containing such sequences and host cells transformed with such expression vectors are also disclosed, as are methods for the expression of the novel VDRR polypeptides of the invention. The invention further relates to VDRR polypeptides for use as medicaments, and use of substances affecting VDRR signal transduction for the manufacture of medicaments for treating metabolic, proliferative or inflammatory conditions. The present invention also relates to methods for identifying clones encoding a VDRR polypeptide, methods for identifying ligands to a VDRR and methods for identifying substances for treatment of conditions affected by a VDRR polypeptide. More specifically, the novel VDRR polypeptide can be the polypeptide designated VDRRγ, which may be regulated by any small chemical molecule similar in structure to known ligands for nuclear receptors.

BRIEF DESCRIPTION OF THE DRAWINGS

FIG. 1—The cDNA sequence encoding the novel nuclear receptor polypeptide vitamin D receptor related gamma (VDRRg) is shown (SEQ ID NO:1).

FIG. 4—The deduced amino acid sequence of VDRRg is shown (SEQ ID NO:2).

FIG. 7—The cDNA sequence encoding VDRRg-2 with an alternatively spliced 5'end compared to VDRRg is shown (SEQ ID NO:3).

FIG. 8—The deduced amino acid sequence of VDRRg-2 is shown (SEQ ID NO:4).

DETAILED DESCRIPTION OF THE INVENTION

The objects above are met by the present invention, which relates to a mammalian, preferably human, isolated or recombinant nucleic acid comprising a contiguous nucleic acid sequence encoding a vitamin D receptor related (VDRR) polypeptide. The VDRR polypeptide is suitably origin.

In preferred embodiments of the present invention, the nucleic acid encoding the VDRR polypeptide contains a DNA-binding domain (DBD) comprising about 77 amino acids with 9 cysteine residues The DBD is further characterized by the following amino acid sequence similarity relative to the DBDs of human Vitamin D Receptor (hVDR) and Orphan Nuclear Receptor 1 isolated from *Xenopus laevis* (xONR1=XOR-6), respectively:

(i) at least about 60% amino acid sequence similarity with the DBD of hVDR, and (ii) at least about 65% amino acid sequence similarity with the DBD of xONR1.

More particularly, the amino acid sequence similarity relative to the DBDs of hVDR and xONR1, respectively is (i) about 65% amino acid sequence similarity with the DBD of hVDR; and
(ii) about 71% amino acid sequence similarity with the DBD of xONR1.

In preferred embodiments of the present invention, the nucleic acid encoding the VDRR polypeptide contains a ligand-binding domain (LBD) characterized by the following amino acid sequence similarity, relative to the LBDs of hVDR and xONR1, respectively:
(i) at least about 30% amino acid sequence similarity with the LBD of hVDR, suitably at least 35% amino acid sequence similarity with the LBD of hVDR; and
(ii) at least about 40% amino acid sequence similarity with the LBD of xONR1, suitably at least 45% amino acid sequence similarity with the LBD of xONR1.

More particularly, the amino acid sequence similarity relative to the LBDs of hVDR and xONR1, respectively is
(i) about 42% amino acid sequence similarity with the LBD of hVDR; and
(ii) about 54% amino acid sequence similarity with the LBD of xONR1.

Figure 13:
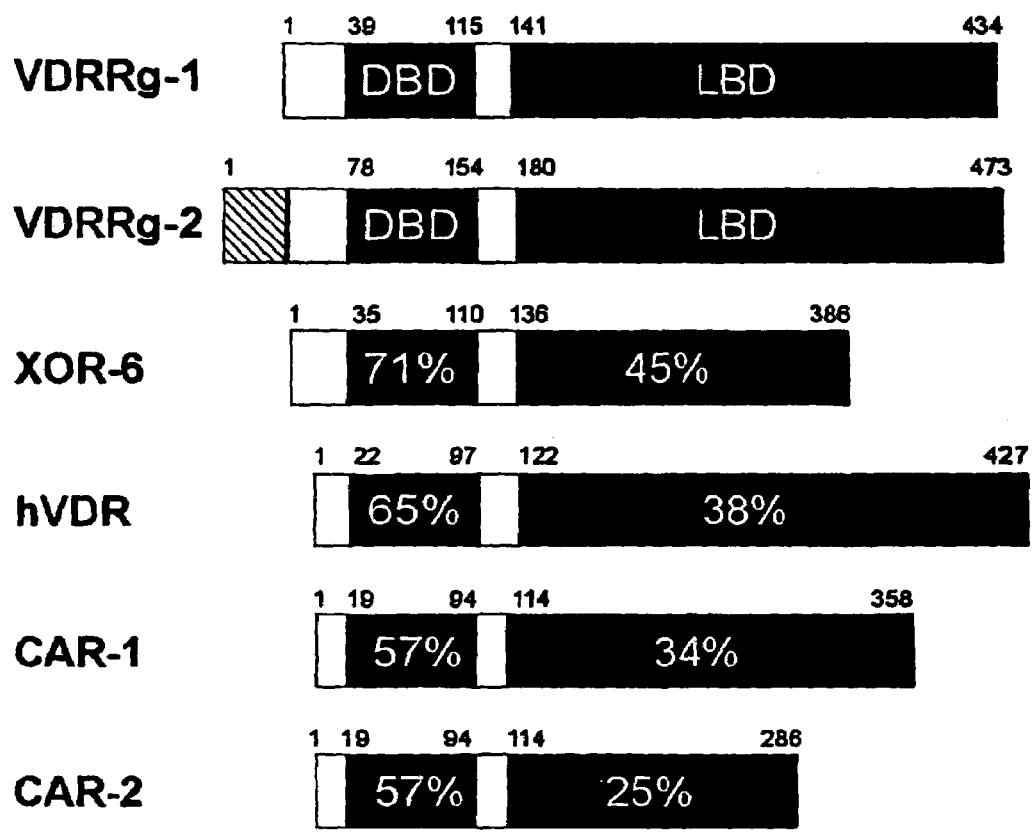
FIG. 13—Percent identity between the new genes VDRRg-1 and VDRRg-2 and the known genes XOR-6. HVDR, CAR-1 and CAR-2.

"amino acid sequence similarity" refers to: 100×Consensus Lenght divided by Consensus Length+Mismatsches+Gaps. The term amino acid sequence identity can also be used. Amino acid sequence identity is calculated by comparing the absolute amino acid residue identity. In FIG. 13 the amino acid sequence identity between the new genes VDRRg-1 and VDRRg-2 and the known genes are shown.

In particularly preferred embodiments, the nucleic acid sequences of the present invention are substatially the same as those given in FIG. 1 (SEQ ID NO:1) or FIG. 7 (SEQ ID NO:3), the same or alleles thereof.

The present invention also relates to a nucleic acid probe for the detection of a nucleic acid sequence encoding a VDRR polypeptide in a sample. Suitably, the probe comprises at least 14 contiguous nucleotides, and preferably at least 28 contiguous nucleotides, of the nucleic acid sequences given in FIG. 1 (SEQ ID NO:1) or FIG. 7 (SEQ ID NO:3). The nucleic acid probe can be used in a method for identifying clones encoding a VDRR polypeptide, wherein the method comprises screening a genomic or cDNA library with the probe under low stringency hybridization conditions, and identifying those clones which display a substantial degree of hybridization to said probe.

The present invention further relates to an isolated or recombinant VDRR polypeptide. The polypeptide can be full-length, at which the sequence of amino acids is identical to the corresponding sequence found in mammals in general, and in human beings in particular. In the present invention, the polypeptide can also be a truncated, extended or mutated form of the full-length polypeptide. Truncated and extended forms relate to VDRR polypeptides where one or more amino acids are missing or have been added, respectively, at the N terminal end of the polypeptide chain. Mutated forms relate to VDRR polypep-tides where one or more amino acid has been substituted by another amino acid. Suitably, the isolated or recombinant VDRR polypeptide exhibits the amino acid sequences given in FIG. 4 (SEQ ID NO:2) or FIG. 8 (SEQ ID NO:4).

The N-terminal sequence of the present nucleic acids encoding VDRR polypeptides, as well as the amino acid sequence of the present VDRR polypeptides, may vary. Thus, various N-terminal isoforms are envisaged, e.g. any of αb 1, α2, β1, β2, β3, β4, γ1 or γ2 as disclosed in FIG. 7B of Transcription Factors 3: nuclear receptors, Protein Profile, vol. 2, issue 11 (1995), pp. 1173–1235. This review of nuclear receptors generally is hereby incorporated by reference. More specifically, Vitamin D receptors and related orphans, e.g. ONR1, are discussed at p. 1191–1992.

The present invention further relates to pharmaceutical formulations comprising an isolated or recombinant VDRR polypeptide, and one or more therapeutically acceptable excipients. Examples of excipients that can be used are carbohydrates, e.g. monosaccharides, disaccharides and sugar alcohols, such as saccharose and sorbitol. Further examples include amino acids, e.g. histidine and arginine, surfactants, e.g. polyoxyethylene sorbitan fatty acid esters, inorganic salts, e.g. sodium chloride and calcium chloride, and complexing agents, e.g. EDTA and citric acid.

The present formulation can be in the form of an aqueous solution ready-for-use, or dried, particularly lyophilized. In the latter case, the formulation is reconstituted with a liquid, e.g. sterile water or saline, before use.

The present invention further relates to an expression vector comprising an isolated or recombinant nucleic acid, the nucleic acid comprising a contiguous nucleic acid sequence encoding a Vitamin D receptor related (VDRR) polypeptide. The invention also relates to a cell containing such an expression vector.

The present invention further relates to a cell containing the claimed nucleic acid, the nucleic acid comprising a contiguous nucleic acid sequence encoding a Vitamin D receptor related (VDRR) polypeptide.

The present invention further relates to a process for recombinant production of a VDRR polypeptide, by expressing the claimed isolated or recombinant contiguous nucleic acid sequence encoding a Vitamin D receptor related (VDRR) polypeptide in a suitable host cell, preferably an eukaryotic cell.

The present invention further relates to method for identifying a ligand to a VDRR, e.g. by a cell-based reporter assay, transgenic-animal reporter assay or in vitro-binding assay. It also relates to a method for identifying a substance for treatment of a condition affected by a VDRR polypeptide, comprising screening for an agonist or an antagonist of VDRR polypeptide signal transduction to be used for treating metabolic, proliferative or inflammatory conditions.

The present invention further relates to a VDRR polypeptide for use as a medicament, as well as use of a substance affecting VDRR signal transduction for the manufac-ture of a medicament for treating metabolic, proliferative or inflammatory conditions. More particularly, the present invention can be used for the manufacture of medicaments for treating obesity, diabetes, anorexia, lipoprotein defects, hyperlipidemia, hypercholeste-remia or hyperlipoproteinemia. The present invention can be used also for the manufacture of medicaments for treating osteoporosis, rheumatoid artritis, benign and malign tumors, hyperproliferative skin disorders or hyperparathyroidism.

The present invention further relates to a method for treating metabolic, proliferative or inflammatory conditions by introducing into a mammal a nucleic acid vector encoding for expression of a VDRR polypeptide. The nucleic acid vector is capable of transforming a cell in vivo and expressing said polypeptide in said transformed cell.

The present invention further relates to a method for treatment of a metabolic, proliferative or inflammatory condition by administration of a therapeutically effective amount of a substance affecting VDRR signal transduction, specifically a VDRR polypeptide.

In the present invention, the term "isolated" in connection with VDRR polypeptides or nucleic acids encoding the same, relates to nucleic acids or polypeptides that have been isolated from a natural source, e.g. the liver, small intestine or colon of a human being. The isolated VDRR polypeptides or nucleic acids of the present invention are unique in the sense that they are not found in a pure or separated form in nature. Use of the term "isolated" indicates that a naturally occurring sequence has been removed from its normal cellular environment. Thus, the sequence may be in a cell-free environment or in a different cellular environment. The term does not imply that the sequence is the only nucleic acid or amino acid sequence present, but that it is the predominant nucleic acid or amino acid sequence present. Furthermore, the nucleic acid or polypeptide should be essentially free of non-amino acid or non-nucleic acid material naturally associated with the respective product. In this context, essentially free relates to more than 80%, suitably more than 90%, and preferably more than 95% purity. The term "sustantially the same" when referring to the nucleic acid sequences in FIG. 1 (SEQ ID NO:1) or FIG. 7 (SEQ ID NO:3) and when referring to the amino acid sequences in FIG. 4 (SEQ ID NO:2) or FIG. 8 (SEQ ID NO:4) means that they are derived from the sequences given in the figures and have the same function as those.

Figure 12:
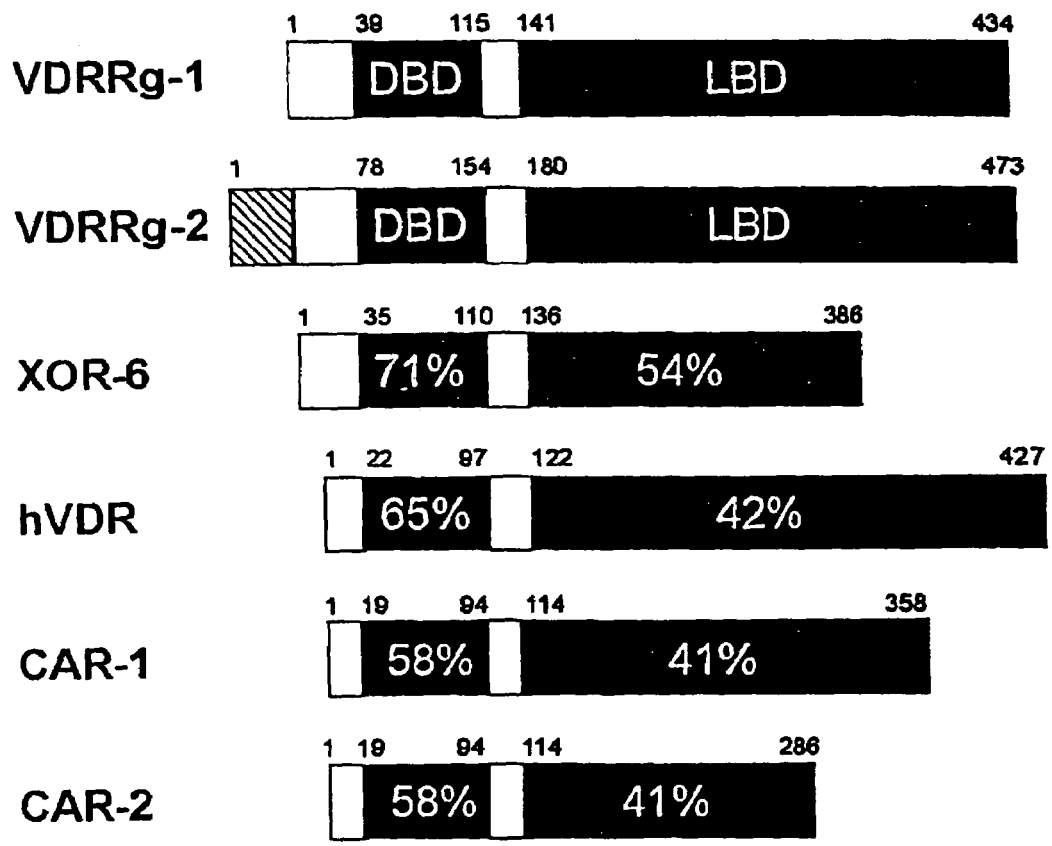
FIG. 12—Percent similarity between the new genes VDRRg-1 and VDRRg-2 and the known genes XOR-6. HVDR, CAR-1 and CAR-2.

The inventors of the present invention, have surprisingly isolated a novel nucleic acid sequence, and a polypeptide encoded by said nucleic acid sequence. Thus, a novel cDNA encoding a polypeptide designated VDRRγ has been cloned and characterized. This polypeptide is, based on amino acid sequence similarity, a novel member of the nuclear (hormone) receptor supergene family. Hidden Markov Models (HMMs) in combination with phylogenetic analysis such as neighbor-joining tree methods and other statistical algorithms shows that VDRRγ belong to a sub-family of vitamin D receptors (VDRs) and a VDR-like receptor from *Xenopus laevis* designated xONR1 (see Smith et al., Nucl. Acids Res., 22 (1994), No. 1, pp. 66–71) or XOR-6 as in WO96/22390. The VDRRγ, therefore, is one member of a family of Vitamin D receptor related (VDRR) polypeptides. The degree of amino acid similarity in the DBD and LBD of VDRRg as compared to the most closely related receptors XOR-6, hVDR and CAR (see WO 93/17041) is similar to the relationship between other distinct, but related nuclear receptors. (See FIG. 12). The thyroid hormone (TRb) and retinoic acid receptor (RARb) are approximately 60% and 40% identical at the amino acid level in the DBD and LBD, respectively. By comparison, the closely related but unique genes encoding human RARa and RARb nuclear receptors are 97% and 82% identical in the DBD and LBD, respectively.

As recognized by those skilled in the art of nuclear receptors, the DBD displays the highest degree of conservation (amino acid identity) both between different nuclear receptors (paralogous) and between identical receptors from different species (orthologues). The two "zink-fingers" in the DBD are generated by two evolutionary conserved amino acid motifs Cys-X2-Cys-X13-Cys-X2-Cys (amino-terminal or first zink-finger) and Cys-Xn-Cys-X9-Cys-X2-Cys (carboxy-terminal or second zink-finger) in which two pairs of cysteins chelate on zink ion. The vast majority of nuclear receptors have five amino acid residues between the firs two Cys residues in the second zink-finger (Cys-X5-Cys-X9-Cys-X2-Cys) see Gronemeyer and Laudet (Protein Profile 1995, 2, issue 11) for details. The today only known exception to this role are the PPARs which have three amino acid (Cys-X3-Cys-X9-Cys-X2-Cys) residues and the TLL group of receptors which have seven (Cys-X7-Cys-X9-Cys-X2-Cys). Thus another feature which is characteristic of the novel VDRRg polypeptide described herein is that the number of amino acid residues in this part of the DBD is six (Cys-X6-Cys-X9-Cys-X2-Cys) as shown in FIGS. 4 and 8. Today, the only other nuclear receptor like sequences found in the TREMBLE data base with the same number of amino acid residues between the two cys residues are two sequences (Q20097 and Q18155) from the worm *C. elegans* (Q20097 and Q18155). However, the entire DBD of these putative *C. elegans* nuclear receptors are only distantly related to the DBD of VDRRg. Taken together, the comparison of the DBD and LBD of the nuclear receptor VDRRg described herein (See FIG. 12), clearly demonstrate that this receptor is a novel member of the nuclear receptor super-gene family which is distinct from other known nuclear receptors that are most closely related to the VDRRg including ONR-1 (in Smith et al., 1994, Nucleic Acids Res., 22, pp66–71) or XOR-6 (in WO 96/22390), hVDR and CAR (WO 93/17041). This finding, in combination with the highly restricted expression pattern we observe for human VDRRγ (liver, small intestine and mucosa of colon) and in analogy to other nuclear receptors exhibiting a tissue specific expression pattern such as the peroxisome pro-liferator-activated receptors (PPARs)—suggest that VDRRγ performs important physiological functions in liver, small intestine and colon. Accordingly, VDRRγ is likely to be an important sensor of key metabolic pathways affecting lipid, carbohydrate or amino acid metabolism/homeostasis. In addition, the highly selective tissue specific expression pattern suggest that VDRRγ may participate in cellular differentiation and development of these tissues.

An additional human VDRRγ cDNA with an alternatively spliced 5'- end has been identified (see FIG. 7 (SEQ ID NO:3)). The VDRRγ cDNAs are thus able to encode at least one alternative N-terminal variant (FIG. 8(SEQ ID NO:4)) in addition to the VDRRγ polypeptide shown in FIG. 4 (SEQ ID NO:2). In analogy to other members of the nuclear receptor supergene family such as RORα and RARα these N-terminal isoforms of VDRRγ may specify different functions including DNA-binding specificity and/or promoter specific activation (Gronemeyer and Laudet, 1995).

In the present specification, the term VDRRγ relates to the various polypeptides corresponding to the differentially spliced VDRRγ cDNAs including VDRRγ-1 and VDRRγ-2. However, when reference is made to FIG. 1 and FIG. 4, (SEQ ID NO:1 and SEQ ID NO:2, respectively), VDRRγ cDNA and VDRRγ relates specifically to VDRRγ-1 cDNA and VDRRγ-1, respectively. In the same way, when reference is made to FIG. 7 and FIG. 8, (SEQ ID NO:3 and SEQ ID NO:4 respectively) VDRRγ cDNA and VDRRγ relates specifically to VDRRγ-2 cDNA and VDRRγ-2, respectively.

In contrast to the VDRRγ-2 cDNA, the VDRRγ-1 cDNA does not contain a classical AUG initiation codon but instead may initiate at an alternative CUG codon. This putative non-AUG start site is located in a favorable sequence context for efficient initiation from alternative start sites and is in frame with the entire open reading frame and preceded by a stop codon.

Taken together, the VDRRs in general, and more specifically the VDRRγ, may be important in
  1) metabolic diseases such as obesity, diabetes (type I and II), lipoprotein disorders,
  2) proliferative conditions such as tumors (benign and malignant) of the small intestine and colon,
  3) ulcero-inflammatory diseases of small intestine and colon such as Crohn's disease and ulcerative colitis, and
  4) congenital anomalies of small intestine and colon.

The high amino acid sequence identity of VDRRγ with the VDR both in the DNA-binding domain (DBD) and ligand-binding domain (LBD) indicate that these two receptors may have overlapping yet distinct functional characteristics. In analogy, retinoic acid receptors (RARs) and retinoid X receptors (RXRs) have similar amino acid sequence identities in the DBD and LBD region as the VDR and VDRRγ. RARs and RXRs have been shown to have distinct functional similarities such that both receptors bind 9-cis retinoic acid and have overlapping DNA-binding specificities and accordingly regulate overlapping gene networks. Based on these findings, VDRRγ may be regulated by small chemical molecules similar in structure to known ligands for nuclear receptors but not necessarily identical to ligands for the 1α, 25-dihydroxy vitamin D3 receptor. Furthermore, VDRRγ may regulate vitamin D3 responsive gene networks by binding to a Vitamin D responsive element (VDRE)-like DNA sequence. In the present application, the 1α, 25-dihydroxy vitamin D3 receptor is abbreviated as the Vitamin D receptor (VDR).

In the present invention, the substance affecting VDRR signal transduction can be any small chemical molecule of natural or synthetic origin, e.g. a carbohydrate such as an aromatic compound. The small molecule may have a molecular weight in the range of from about 100 up to about 500 Da. Suitably, the small chemical molecule has a molecular weight in the range of from 200 up to 400 Da. Preferably, the small chemical molecule has a molecular weight of about 300 Da.

The human VDRRγ polypeptides, including VDRRγ-1 and VDRRγ-2, have been shown to be activated e.g. by pregnenolones and estradiol (weakly), but not by certain other steroid hormones such as cortisol, aldosterone, progesterone and estrogen, and most likely not by progestines and glucocorticoids. Thus, human VDRRγ is not activated by pregnenolone 16α-carbonitrile (PCN), a glucocorticoid antagonist. For his reason, human VDRRγ can also be designated human pregnenolone activated (nuclear) receptors (hPAR). Information about pregnenolone can be found e.g. in the Merck Index, 11th ed., Merck & Co., Inc. Rahway, N.J., USA, p 7735, 1989.

Activators for human VDRRγ polypeptides, including VDRRγ-1 and VDRRγ-2, (hPAR-1 and hPAR-2, respectively), include but are not limited to pregnenolones, such as pregnane-ones, pregnane-diones, pregnane-triones, and pregnane-diols, and androstanes, such as androstane-ols, and androstane-diols. Suitably, the pregnenolones are non-planar, particularly 5β-pregnanes.

Specific examples of activators and possibly ligands for human VDRRγ polypeptides, including VDRRγ-1 and VDRRγ-2, are the following compounds, which are marketed by Sigma-Aldrich of Sweden:

i) 5β-pregnane-3,20-dione
ii) 3α-hydroxy-5β-pregnane-11,20-dione methanesulphonate
iii) 5β-pregnane-3α,20β-diol
iv) pregnenolone
v) Pregn-4-eno[16,17-δ][2]isoxazolline-3,20-dione, 6α-methyl-3'-phenyl-, ethyl ether solvate
vi) Pregna-1,4,9(11)-triene-3,20-dione, 21-[4-[6-methoxy-2-(4-morpholinyl)-4-pyrimidinyl]-1-piperazinyl]-16-methyl-, (16α)-
vii) Estran-3-ol, 17-[[[3-(trifluoromethyl)phenyl]methyl]amino]-, (E)-2-butenedioate (1:1) (salt)
viii) 9α-Fluoro-5α-androstane-11β,17β-diol
ix) Spiro[-5α-androstane-3,2'-benzothiazolin]-11-one, 17β-hydroxy-17-methyl-,
x) Spiro[pregnane-3,2'-thiazolidine]-4'-carboxylic acid, 11α-hydroxy-20-oxo-, sodium salt
xi) 17β-Dimethylamino-17-ethynyl-5α-androstane-11β-ol
xii) 6β-Hydroxy-3,5-cyclo-5α-pregnan-20-one, nitrite
xiii) 3α-Hydroxy-5β-pregnane-11,20-dione, acetate, 20-O-(methylsulfonyl)-oxime
xiv) 17α-Methyl-5α-androstane-11β,17-diol
xv) 5β-Pregnane-3,11,20-trione, trioxime
xvi) 3α-Hydroxy-5β-pregnane-11,20-dione, 20-hydazone with hydrazide of 1-(carboxymethyl)pyridinium chloride.

A possible use of a VDRRg antagonist, could be a synergistic co-administration of the VDRRg antagonist together with other drugs such as, but not limited to, HIV protease inhibitors and cyclosporin to inhibit the expression of CYP3A4 and thus increase the bioavailability of drugs with poor pharmacokinetics due to CYP3A4 metabolism. Genes coding for polypeptides, such as human vitamin D receptor related gamma (hVDRRg), may be cloned by incorporating a DNA fragment coding for the polypeptide into a recombinant DNA vehicle, e.g. a vector, and transforming suitable prokaryotic or eukaryo-tic host cells. Such recombinant DNA techniques are well known and e.g. described in Methods in Enzymology, Academic Press, San Diego, Calif., USA (1994), vols. 65 and 68 (1979), and vols. 100 and 101 (1983).

The host cells for use in the present invention can be prokaryotic or eukaryotic, preferably eukaryotic cells. Suitable eukaryotic bost cells include but are not limited to cells from yeast, e.g. *Saccharomyces*, insect cells and mammalian cells such as Chinese Hamster Ovary (CHO), Baby Hamster Kidney (BHK), COS and the like. Suitable prokaryotic host cells include but are not limited to cells from *Enterobacteriacea*, e.g. *E. coli, Bacillus* and *Streptomyces*.

EXAMPLES

The following Examples are provided for purposes of illustration only and are not to be construed as in any way limiting the scope of the present invention, which is defined by the appended claims.

Example 1

Identification and Isolation of Human VDRRg cDNA

Expressed Sequence Tag (EST) databases were screened for nuclear receptor related sequences with a DNA-binding domain (DBD) profile of nuclear receptors. This search profile was created by multiple alignment of a selected set of nuclear receptor sub-domains followed by a statistical calculation to obtain a so called Hidden Markov Model (HMM) of different subfamily members of the nuclear receptor supergene family. The cDNA of one of the nuclear receptor related EST sequences identified (Incyte clone no 2211526) was analyzed in detail by sequencing. After DNA sequencing of the entire Incyte cDNA clone (approximately 2200 basepairs) the clone was found to encode a putative ligand-binding domain (LBD) with 54% and 44% similarity to xONR-1 and to the vitamin D receptor (VDR), respectively. The cDNA of the Incyte clone was not full-length and did not encode a sequence corresponding to a complete DBD.

Figure 2:
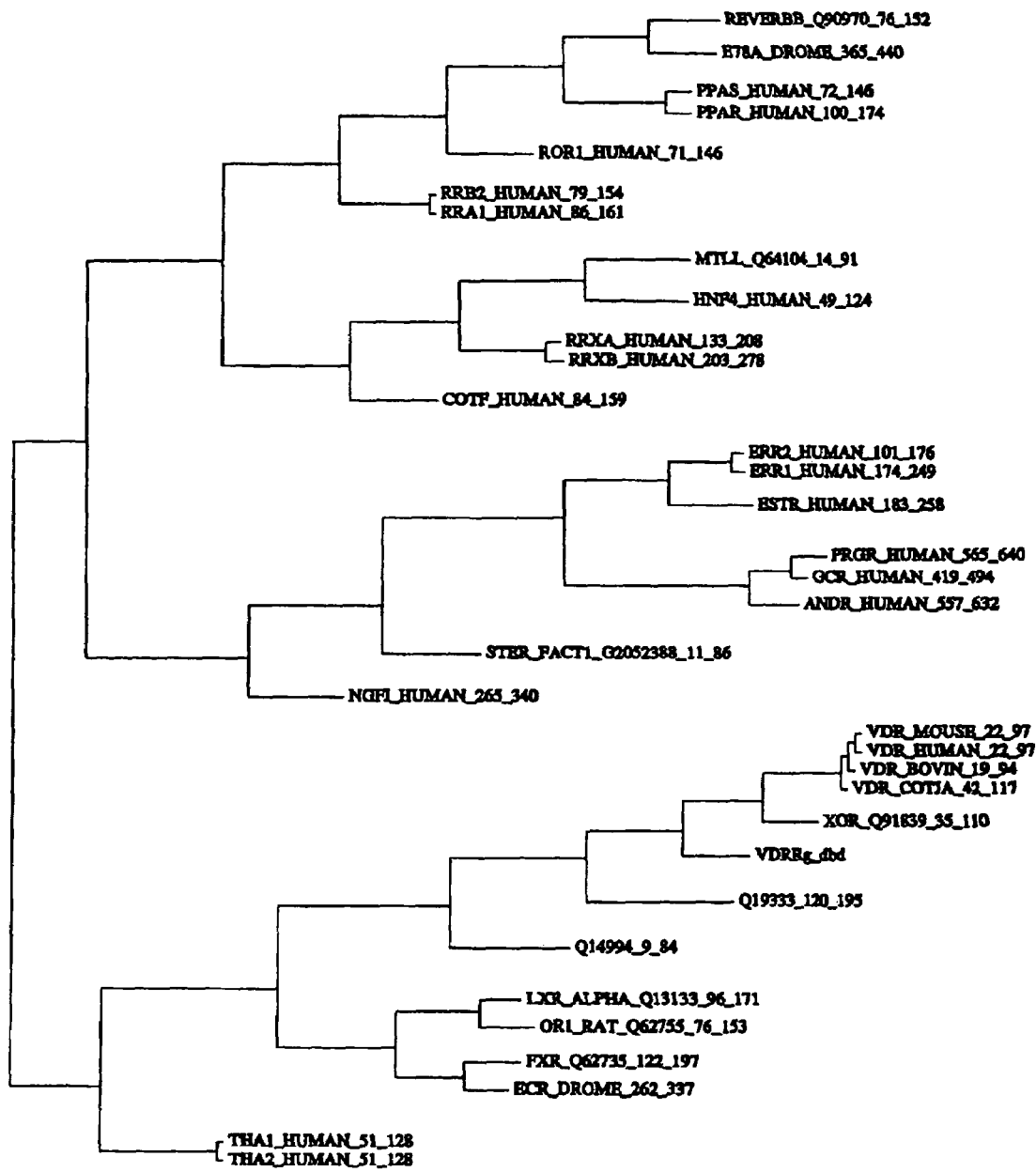
FIG. 2—Evolutionary neighbor-joining tree for VDRRg as given by DBD-HMM alignment.
Figure 3:
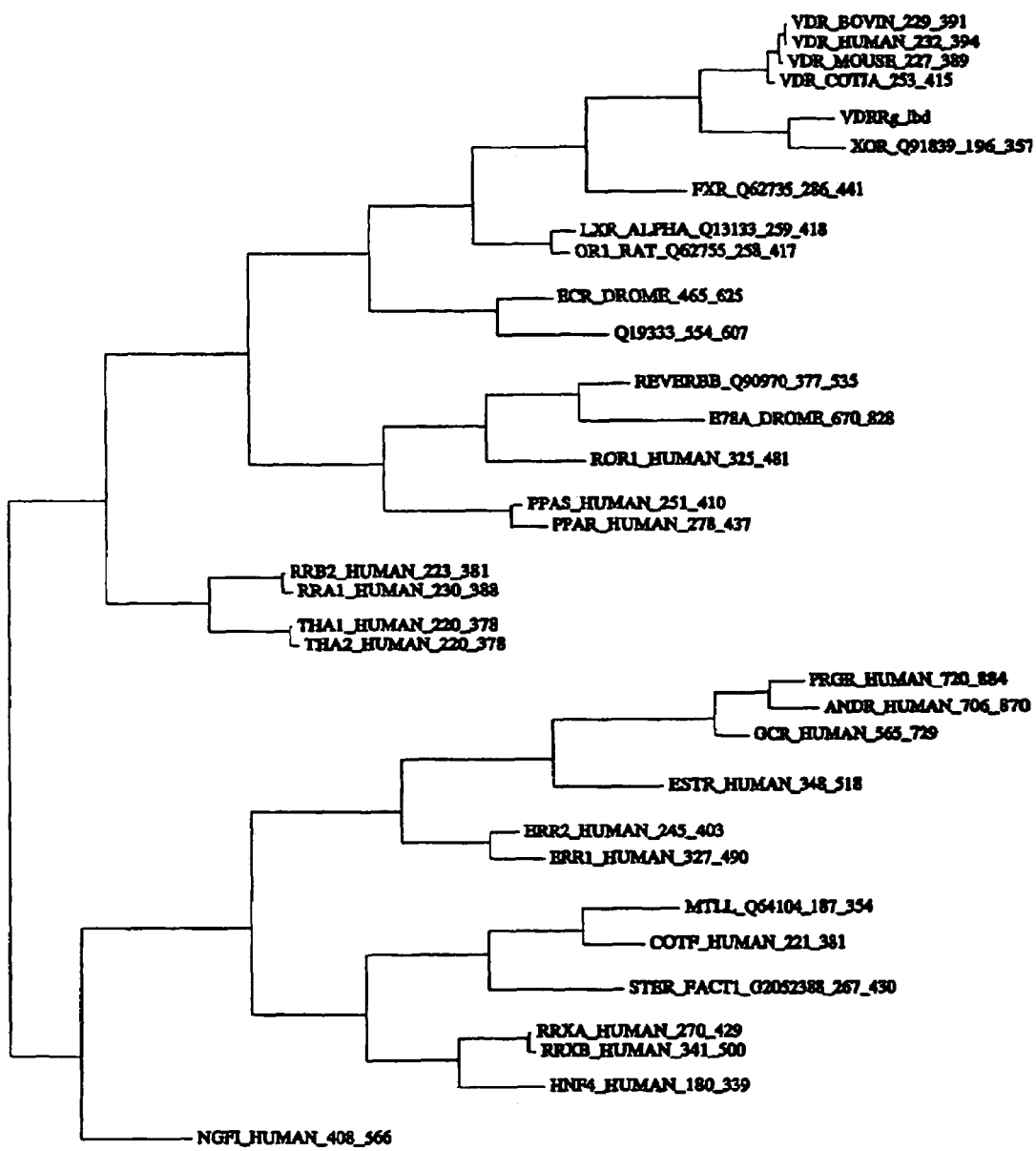
FIG. 3—Evolutionary neighbor-joining tree for VDRRg as given by LBD-HMM alignment.

5'-RACE (rapid amplification of cDNA ends) of random primed cDNA from human liver RNA (InVitrogen) followed by cloning and DNA sequencing showed that the 5'-part of the cDNA corresponding to the Incyte clone encoded a DBD characteristic for nuclear receptors and with 71% and 65% sequence similarity to xONR-1 and VDR, respectively. Multiple alignments in combination with evolutionary neighbor-joining tree analysis placed the polypeptide encoded by the cDNA (specified in FIG. 1) in the group of VDRs (FIGS. 2 and 3) and was named human vitamin D receptor related gamma (VDRRg). The deduced amino acid sequence of VDRRg is given in FIG. 4 (SEQ ID NO:2).

Example 2

Expression of VDRRg mRNA in Human Tissues

Figure 5:
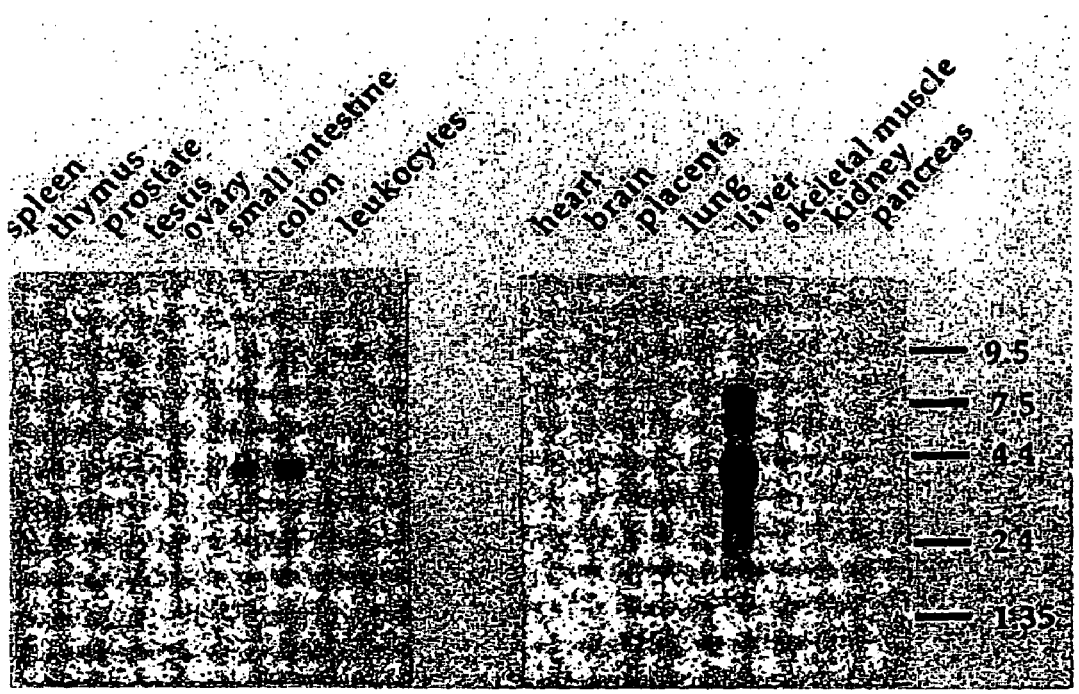
FIG. 5—Expression of VDRRg in adult human tissues. The numbers on the right hand side, refer to kilobasepairs of the mRNA.

Multiple tissue northern blots (Clontech) was used to determine the expression pattern of VDRRg in adult human tissues. As shown in FIG. 5, VDRRg is abundantly expressed in small intestine, mucosal lining of colon and liver but not in several other tissues including spleen, thymus, prostate, testis, ovary, peripheral blood leukocytes, heart, brain, placenta, lung, skeletal muscle, kidney and pancreas. To investigate if VDRRγ was expressed at lower levels in any of the other tissues examined, the filter was exposed for an extended time (one week as compared to overnight). Even after this prolonged exposure (data not shown), expression could still only be detected in the same tissues and not in any of the other tissues examined. The restricted expression pattern of VDRRg suggest that this receptor is likely to have an important regulatory function in liver and intestine.

Example 3

Transient Transfections of GAL4-DBD/VDRRγ-LBD Fusion Protein Using Vitamin D3

Figure 6:
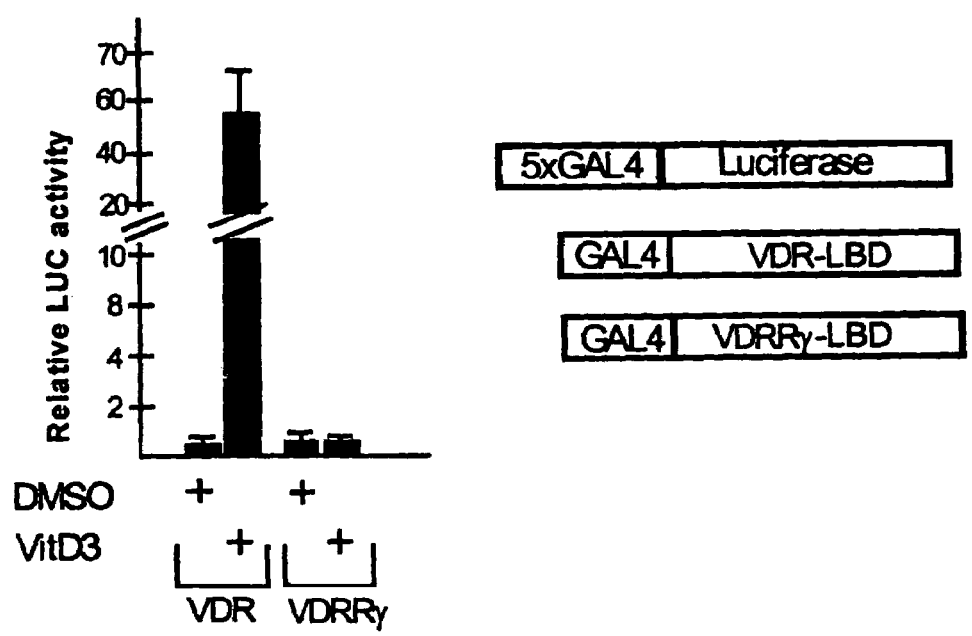
FIG. 6—Vitamin D3 transactivate a GAL4-DBD/VDR-LBD fusion protein but not a GAL4-DBD/VDRRγ-LBD fusion protein in transient transfections of CV-1 cells. The number on the left hand side refer to relative luciferase activity of the GAL4-luciferase reporter gene.

Transient transfections were performed to analyze if vitamin D3 activate the VDRRγ polypeptide. To this end, transient co-tansfections of CV-1 cells were performed with expression plasmids encoding fusion proteins of the GAL4-DBD fused to the LBD of either the VDR or the VDRR together with a reporter-plasmid containing five GAL4 responsive elements upstream of the luciferase gene. After transfection, cells were treated with vehicle (DMSO) alone or with vitamin D3 for 48 hours followed by harvesting of the cells and measurement of the luciferase activity in cell extracts. As shown in FIG. 6, vitamin D3 (1 µM) transactivate the GAL4-DBD/VDR-LBD but not the corresponding GAL4-DBD/VDRRγ-LBD polypeptide under these conditions. This indicates that the two receptors may have distinct ligand-binding specificities.

Example 4

Identification and Isolation of Human VDRRγ cDNAs Encoding Multiple N-terminal Isoforms 5'-RACE (see Example 1) of cDNA from human liver RNA followed by cloning and DNA sequencing identified an additional human VDRRγ cDNA with alternatively spliced 5'-end (see FIG. 7 (SEQ ID NO:3)). The VDRRγ cDNAs are thus able to encode at least one alternative N-terminal variant (FIG. 8 (SEQ ID NO:4)) in addition to the VDRRγ polypeptide shown in FIG. 4 (SEQ ID NO:2). The polypeptides disclosed in FIG. 4 and FIG. 8 (SEQ ID NO:2 and SEQ ID NO:4, respectively), which correspond to the differentially spliced VDRRγ cDNAs are designated as VDRRγ-1 and VDRRγ-2, respectively.

Example 5

Figure 9:
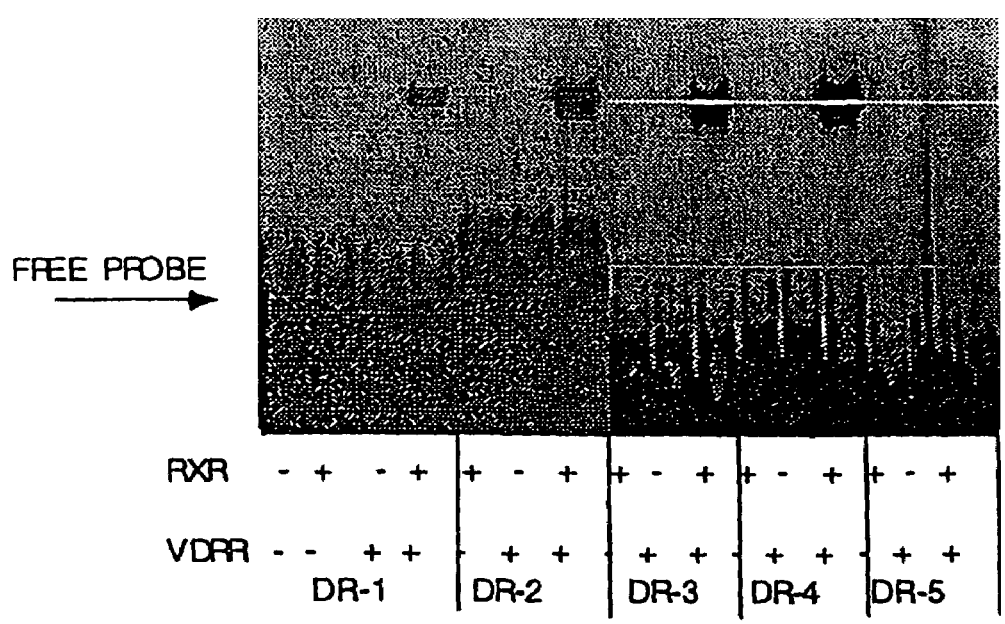
FIG. 9—Heterodimerization of VDRRg with a retinoid X receptor (RXR) is shown.

VDRRγ Heterodimerise with RXR and Bind to Direct Repeats (DRs) Spaced by Three or Four Nucleotides Expression plasmids containing VDRRγ or RXRβ cDNAs were transcribed using T7 polymerase and translated in vitro in TNT reticulocyte lysates (Promega, Madison, Wis., USA). To investigate the DNA-binding specificity of VDRRγ a native gel mobility assay was employed essentially as described (Berkenstam et al., Cell, 69, 401–412, 1992) in which in vitro translated VDRRγ was incubated in the presence or absence of in vitro translated RXRβ with different 32P-labelled direct repeats (DR-1 to DR-5) as indicated in FIG. 9. The direct repeats were derived from the DR-5 element in the RAR-β2 promoter (de Thé et al., Nature, 343, 177–180, 1990) and modified to be separated by one to five nucleotides (Pettersson et al., Mechanisms of Dev., 54, 1–13, 1995). Protein-DNA complexes were separated on native 5% polyacryl-amide/0.25×TBE gels followed by autoradiography. As shown in FIG. 9, of the five DRs tested efficient VDRRγ binding could only be detected with DRs separated by three or four nucleotides and only in the presence of RXR. However, weaker RXR-dependent binding could also be observed to DR-2 and DR-1 elements. These results demonstrate that VDRRγ require RXR heterodimerisation for efficient DNA-binding to a specific subset of DRs. These results, however, do not exclude the possibility that VDRRγ may bind as a monomer, dimer or heterodimer to distinct but related DNA-sequences. Importantly, our results demonstrate that VDRRγ and other nuclear receptors including the VDR (e.g. Markose, E. R. et al., Proc. Natl. Acad. Sci. USA, 87, 1701–1705, 1990), THRs (erg Gronemeyer, H. and Moras, D., Nature, 375, 190–191, 1995), LXRs (e.g. Willy, P. J. et al., Genes. Dev., 9, 1033–1045, 1995), have distinct but overlapping DNA-sequence and thus may regulate overlapping gene networks. Interestingly, the most closely related nuclear receptor called ONR-1 (in Smith et al., 1994, Nucleic Acids Res., 22, pp66–71) or XOR-6 (in WO 96/22390) have been reported to "bind well to a retinoic acid response element, bRARE" (p. 11, line 30 in WO 96/22390). However, although the novel nuclear receptor VDRRg reported herein has 71% amino acid similarity in the DBD as compared to XOR-6 (FIG. 12), VDRRg does not appear to bind to the same bRARE sequence (DR-5 in FIG. 9).

Example 6

Pregnenolone Derivatives as Activators of VDRRγ

Figure 10:
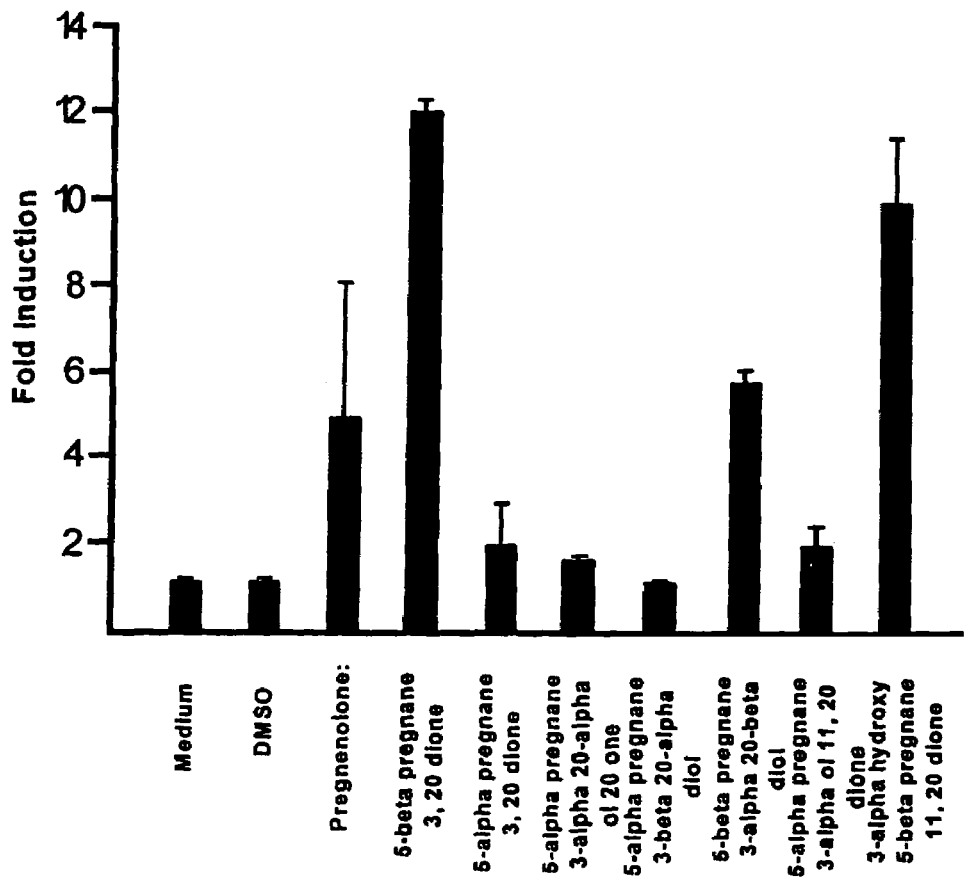
FIG. 10—The effect of pregnenolone derivatives as activators of VDRRg are shown.

For identifying activators or ligands for VDRRγ, a library of substances structurally biased towards different classes of activators and ligands for nuclear receptors were tested. The activation of VDRRγ was analyzed in a reporter gene assay in transiently Caco-2 (TC7) cells (Carriere et al, 1994). In this initial screen, the synthetic substances with ability to activate VDRRγ were found to be structurally similar to pregnenolones (data not shown). Based on these results, naturally occuring pregnenolone derivatives were examined for activation of VDRRγ. The results are shown in FIG. 10. As is evident from FIG. 10, VDRRγ was activated about 5 to 12 fold by pregnenolone, 5β-pregnane-3,20-dione, 5β-pregnane-3α,20β-diol and 3α-hydroxy-5β-pregnane-11, 20-dione methanesulphonate. In contrast to the efficient activation observed by the 5β-pregnane-3,20-dione, the corresponding planar steroid derivative 5α-pregnane-3,20-dione did not activate the receptor. Other 5β-pregnanes also activated VDRRγ efficiently as opposed to all planar pregnenolone derivatives tested, as is also evident from FIG. 10.

Example 7

Figure 11:
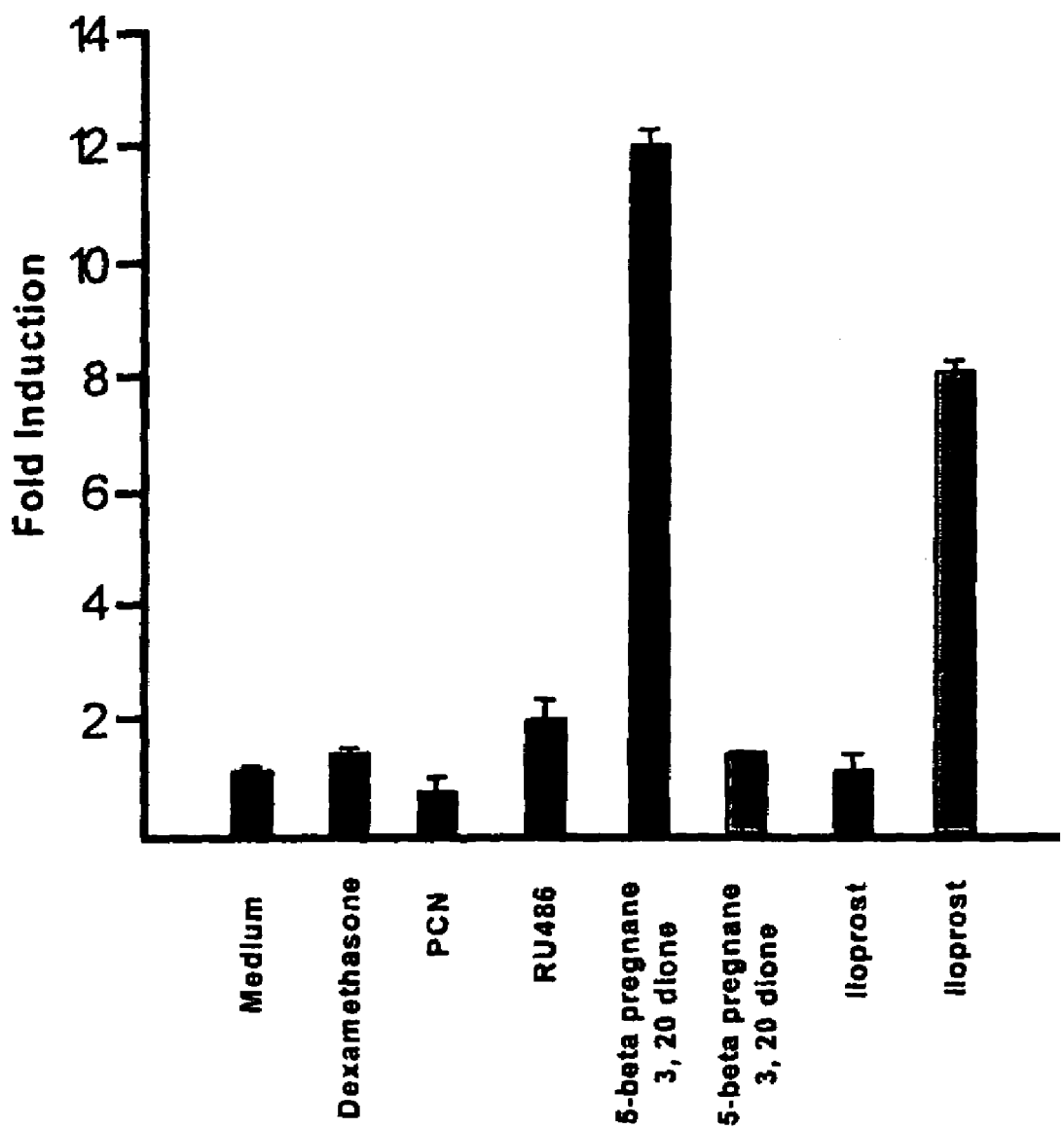
FIG. 11—The effect of pregnenolone 16α-carbonitrile (PCN), dexamethasone and an antiprogestin (RU486) as activators of VDRRg are shown.

Pregnenolone 16α-carbonitrile (PCN), Dexamethasone and an Antiprogestin (RU486) as Activators of VDRRg Further experiments were performed to find out if pregnenolone 16α-carbonitrile (PCN), a glucocorticoid antagonist or dexamethasone are activators of VDRRγ. To this effect, Caco-2 cells were transfected as before with VDRRγ and the activation was analyzed after treatment of the cells with 10 μM PCN or dexamethasone. The results are shown in FIG. 11. As is evident from FIG. 11, VDRRγ was not activated by these substances, indicating that VDRRγ is not the human PCN receptor. This suggestion is corroborated by the observation that also the antiprogestin RU486 only caused a slight increase (two fold) in VDRRγ mediated reporter gene activity as is evident from FIG. 11. Activators of XOR-6 (FIG. 3 in WO 96/22390) such as butyl 4-NH2 Benzoate did not activate VDRRg (data not shown) in similar reporter assays as used in WO 96/22390.

The invention claimed is:

1. An isolated nucleic acid comprising the nucleotide sequence of SEQ ID NO:1.

2. A process for producing a polypeptide of SEQ ID NO:2 the process comprising:
   (a) culturing a cell which has been transformed with a recombinant polynucleotide that comprises a promoter sequence operably linked to a polynucleotide of claim 1 under conditions suitable for the expression of the polypeptide, and
   (b) recovering the expressed polypeptide.

3. The process of claim 2, wherein the host cell is eukaryotic.

4. An expression vector comprising the nucleic acid of claim 1.

5. An isolated cell containing the expression vector of claim 4.

* * * * *

SEQUENCE LISTING

<160> NUMBER OF SEQ ID NOS: 4

<210> SEQ ID NO 1
<211> LENGTH: 2905
<212> TYPE: DNA
<213> ORGANISM: Artificial Sequence
<220> FEATURE:
<223> OTHER INFORMATION: Description of Artificial Sequence: [cDNA of
      encoding sequence of vitamin D receptor related gamma (VDRRg)]

<400> SEQUENCE: 1

```
cctctgaagg ttctagaatc gatagtgaat tcgtgggacg ggaagaggaa gcactgcctt      60
tacttcagtg ggaatctcgg cctcagcctg caagccaagt gttcacagtg aaaaaagcaa     120
gagaataagc taatactcct gtcctgaaca aggcagcggc tccttggtaa agctactcct     180
tgatcgatcc tttgcaccgg attgttcaaa gtggacccca ggggagaagt cggagcaaag     240
aacttaccac caagcagtcc aagaggccca gaagcaaacc tggaggtgag acccaaagaa     300
agctggaacc atgctgactt tgtacactgt gaggacacag agtctgttcc tggaaagccc     360
agtgtcaacg cagatgagga agtcggaggt ccccaaatct gccgtgtatg tggggacaag     420
gccactggct atcacttcaa tgtcatgaca tgtgaaggat gcaagggctt tttcaggagg     480
gccatgaaac gcaacgcccg gctgaggtgc cccttccgga agggcgcctg cgagatcacc     540
cggaagaccc ggcgacagtg ccaggcctgc cgcctgcgca agtgcctgga gagcggcatg     600
aagaaggaga tgatcatgtc cgacgaggcc gtggaggaga ggcgggcctt gatcaagcgg     660
aagaaaagtg aacggacagg gactcagcca ctgggagtgc aggggctgac agaggagcag     720
cggatgatga tcagggagct gatggacgct cagatgaaaa cctttgacac taccttctcc     780
catttcaaga atttccggct gccaggggtg cttagcagtg gctgcgagtt gccagagtct     840
ctgcaggccc catcgaggga agaagctgcc aagtggagcc aggtccggaa agatctgtgc     900 tcttgaagg tctctctgca gctgcggggg gaggatggca gtgtctggaa ctacaaaccc     960
ccagccgaca gtgcgggaa agagatcttc tccctgctgc cccacatggc tgacatgtca    1020
acctacatgt tcaaaggcat catcagcttt gccaaagtca tctcctactt cagggacttg    1080
cccatcgagg accagatctc cctgctgaag ggggccgctt cgagctgtg tcaactgaga    1140 ttcaacacag tgttcaacgc ggagactgga acctgggagt gtggccggct gtcctactgc    1200
ttggaagaca ctgcaggtgg cttccagcaa cttctactgg agcccatgct gaaattccac    1260
tacatgctga agaagctgca gctgcatgag gaggagtatg tgctgatgca ggccatctcc    1320
ctcttctccc cagaccgccc aggtgtgctg cagcaccgcg tggtggacca gctgcaggag    1380
caattcgcca ttactctgaa gtcctacatt gaatgcaatc ggccccagcc tgctcatagg    1440
ttcttgttcc tgaagatcat ggctatgctc accgagctcc gcagcatcaa tgctcagcac    1500
```

-continued

```
acccagcggc tgctgcgcat ccaggacata caccccttg ctacgcccct catgcaggag      1560
ttgttcggca tcacaggtag ctgagcggct gcccttgggt gacacctccg agaggcagcc      1620
agacccagag ccctctgagc cgccactccc gggccaagac agatggacac tgccaagagc      1680
cgacaatgcc ctgctggcct gtctccctag ggaattcctg ctatgacagc tggctagcat      1740
tcctcaggaa ggacatgggt gccccccacc cccagttcag tctgtaggga gtgaagccac      1800
agactcttac gtggagagtg cactgacctg taggtcagga ccatcagaga ggcaaggttg      1860 cccttcctt ttaaaaggcc ctgtggtctg gggagaaatc cctcagatcc cactaaagtg       1920
tcaaggtgtg gaagggacca agcgaccaag gataggccat ctggggtcta tgcccacata      1980
cccacgtttg ttcgcttcct gagtcttttc attgctacct ctaatagtcc tgtctcccac      2040
ttcccactcg ttcccctcct cttccgagct gctttgtggg ctcaaggcct gtactcatcg      2100
gcaggtgcat gagtatctgt gggagtcctc tagagagatg agaagccagg aggcctgcac      2160
caaatgtcag aagcttggca tgacctcatt ccggccacat cattctgtgt ctctgcatcc      2220
atttgaacac attattaagc actgataata ggtagcctgc tgtggggtat acagcattga      2280
ctcagatata gatcctgagc tcacagagtt tatagttaaa aaaacaaaca gaaacacaaa      2340
caatttggat caaaggaga aaatgataag tgacaaagc agcacaagga atttccctgt       2400
gtggatgctg agctgtgatg gcaggcactg ggtacccaag tgaaggttcc cgaggacatg      2460
agtctgtagg agcaagggca caaactgcag ctgtgagtgc gtgtgtgtga tttggtgtag      2520
gtaggtctgt ttgccacttg atggggcctg ggtttgttcc tggggctgga atgctgggta      2580
tgctctgtga caaggctacg ctgacaatca gttaaacaca ccggagaaga accatttaca      2640
tgcaccttat atttctgtgt acacatctat tctcaaagct aaagggtatg aaagtgcctg      2700
ccttgtttat agccacttgt gagtaaaaat ttttttgcat tttcacaaat tatactttat      2760
ataaggcatt ccacacctaa gaactagttt tgggaaatgt agccctgggt ttaatgtcaa      2820
atcaaggcaa aaggaattaa ataatgtact tttggctaaa aaaaaaaaa aaaaaaaaa      2880 aaaaaaaaa aaaaaaaaa aaaaa                                              2905
```

<210> SEQ ID NO 2
<211> LENGTH: 434
<212> TYPE: PRT
<213> ORGANISM: Artificial Sequence
<220> FEATURE:
<223> OTHER INFORMATION: Description of Artificial Sequence: [Deduced amino acid sequence of vitamin D receptor related gamma (VDRRg)]

<400> SEQUENCE: 2

```
Met Glu Val Arg Pro Lys Glu Ser Trp Asn His Ala Asp Phe Val His
  1               5                  10                  15

Cys Glu Asp Thr Glu Ser Val Pro Gly Lys Pro Ser Val Asn Ala Asp
             20                  25                  30

Glu Glu Val Gly Gly Pro Gln Ile Cys Arg Val Cys Gly Asp Lys Ala
         35                  40                  45

Thr Gly Tyr His Phe Asn Val Met Thr Cys Glu Gly Cys Lys Gly Phe
     50                  55                  60

Phe Arg Arg Ala Met Lys Arg Asn Ala Arg Leu Arg Cys Pro Phe Arg
 65                  70                  75                  80

Lys Gly Ala Cys Glu Ile Thr Arg Lys Thr Arg Arg Gln Cys Gln Ala
                 85                  90                  95

Cys Arg Leu Arg Lys Cys Leu Glu Ser Gly Met Lys Lys Glu Met Ile
```

```
                  100                 105                 110
Met Ser Asp Glu Ala Val Glu Glu Arg Arg Ala Leu Ile Lys Arg Lys
        115                 120                 125

Lys Ser Glu Arg Thr Gly Thr Gln Pro Leu Gly Val Gln Gly Leu Thr
    130                 135                 140

Glu Glu Gln Arg Met Met Ile Arg Glu Leu Met Asp Ala Gln Met Lys
145                 150                 155                 160

Thr Phe Asp Thr Thr Phe Ser His Phe Lys Asn Phe Arg Leu Pro Gly
                165                 170                 175

Val Leu Ser Ser Gly Cys Glu Leu Pro Glu Ser Leu Gln Ala Pro Ser
            180                 185                 190

Arg Glu Glu Ala Ala Lys Trp Ser Gln Val Arg Lys Asp Leu Cys Ser
        195                 200                 205

Leu Lys Val Ser Leu Gln Leu Arg Gly Glu Asp Gly Ser Val Trp Asn
    210                 215                 220

Tyr Lys Pro Pro Ala Asp Ser Gly Gly Lys Glu Ile Phe Ser Leu Leu
225                 230                 235                 240

Pro His Met Ala Asp Met Ser Thr Tyr Met Phe Lys Gly Ile Ile Ser
                245                 250                 255

Phe Ala Lys Val Ile Ser Tyr Phe Arg Asp Leu Pro Ile Glu Asp Gln
            260                 265                 270

Ile Ser Leu Leu Lys Gly Ala Ala Phe Glu Leu Cys Gln Leu Arg Phe
        275                 280                 285

Asn Thr Val Phe Asn Ala Glu Thr Gly Thr Trp Glu Cys Gly Arg Leu
    290                 295                 300

Ser Tyr Cys Leu Glu Asp Thr Ala Gly Gly Phe Gln Gln Leu Leu Leu
305                 310                 315                 320

Glu Pro Met Leu Lys Phe His Tyr Met Leu Lys Lys Leu Gln Leu His
                325                 330                 335

Glu Glu Glu Tyr Val Leu Met Gln Ala Ile Ser Leu Phe Ser Pro Asp
            340                 345                 350

Arg Pro Gly Val Leu Gln His Arg Val Val Asp Gln Leu Gln Glu Gln
        355                 360                 365

Phe Ala Ile Thr Leu Lys Ser Tyr Ile Glu Cys Asn Arg Pro Gln Pro
    370                 375                 380

Ala His Arg Phe Leu Phe Leu Lys Ile Met Ala Met Leu Thr Glu Leu
385                 390                 395                 400

Arg Ser Ile Asn Ala Gln His Thr Gln Arg Leu Leu Arg Ile Gln Asp
                405                 410                 415

Ile His Pro Phe Ala Thr Pro Leu Met Gln Glu Leu Phe Gly Ile Thr
            420                 425                 430

Gly Ser
```

<210> SEQ ID NO 3
<211> LENGTH: 2802
<212> TYPE: DNA
<213> ORGANISM: Artificial Sequence
<220> FEATURE:
<223> OTHER INFORMATION: Description of Artificial Sequence: [cDNA of encoding sequence of vitamin D receptor related gamma-2 (VDRRg-2)]

<400> SEQUENCE: 3

```
tgaattcgtg ggcctgctgg gttagtgctg gcagcccccc tgaggccaag gacagcagca      60
tgacagtcac caggactcac cacttcaagg agggtccct cagagcacct gccatacccc     120
```

-continued

| | |
|---|---|
| tgcacagtgc tgcggctgag ttggcttcaa accatccaag aggcccagaa gcaaacctgg | 180 |
| aggtgagacc caaagaaagc tggaaccatg ctgactttgt acactgtgag gacacagagt | 240 |
| ctgttcctgg aaagcccagt gtcaacgcag atgaggaagt cggaggtccc caaatctgcc | 300 |
| gtgtatgtgg ggacaaggcc actggctatc acttcaatgt catgacatgt gaaggatgca | 360 |
| agggcttttt caggagggcc atgaaacgca acgcccggct gaggtgcccc ttccggaagg | 420 |
| gcgcctgcga gatcacccgg aagacccggc gacagtgcca ggcctgccgc ctgcgcaagt | 480 |
| gcctggagag cggcatgaag aaggagatga tcatgtccga cgaggccgtg gaggagaggc | 540 |
| gggccttgat caagcggaag aaaagtgaac ggacagggac tcagccactg ggagtgcagg | 600 |
| ggctgacaga ggagcagcgg atgatgatca gggagctgat ggacgctcag atgaaaacct | 660 |
| ttgacactac cttctcccat ttcaagaatt tccggctgcc aggggtgctt agcagtggct | 720 |
| gcgagttgcc agagtctctg caggcccat cgagggaaga agctgccaag tggagccagg | 780 |
| tccgaaaga tctgtgctct tgaaggtct ctctgcagct gcgggggag gatggcagtg | 840 |
| tctggaacta caaaccccca gccgacagtg gcgggaaaga gatcttctcc ctgctgcccc | 900 |
| acatggctga catgtcaacc tacatgttca aaggcatcat cagctttgcc aaagtcatct | 960 |
| cctacttcag ggacttgccc atcgaggacc agatctccct gctgaagggg gccgctttcg | 1020 |
| agctgtgtca actgagattc aacacagtgt caacgcgga gactggaacc tgggagtgtg | 1080 |
| gccggctgtc ctactgcttg aagacactg caggtggctt ccagcaactt ctactggagc | 1140 |
| ccatgctgaa attccactac atgctgaaga gctgcagct gcatgaggag gagtatgtgc | 1200 |
| tgatgcaggc catctcctc ttctccccag accgcccagg tgtgctgcag caccgcgtgg | 1260 |
| tggaccagct gcaggagcaa ttcgccatta ctctgaagtc ctacattgaa tgcaatcggc | 1320 |
| cccagcctgc tcataggttc ttgttcctga agatcatggc tatgctcacc gagctccgca | 1380 |
| gcatcaatgc tcagcacacc cagcggctgc tgcgcatcca ggacatacac ccctttgcta | 1440 |
| cgcccctcat gcaggagttg ttcggcatca caggtagctg agcggctgcc cttgggtgac | 1500 |
| acctccgaga ggcagccaga cccagagccc tctgagccgc cactcccggg ccaagacaga | 1560 |
| tggacactgc caagagccga caatgccctg ctggcctgtc tccctaggga attcctgcta | 1620 |
| tgacagctgg ctagcattcc tcaggaagga catgggtgcc ccccaccccc agttcagtct | 1680 |
| gtagggagtg aagccacaga ctcttacgtg gagagtgcac tgacctgtag gtcaggacca | 1740 |
| tcagagaggc aaggttgccc tttccttta aaaggccctg tggtctgggg agaaatccct | 1800 |
| cagatcccac taaagtgtca aggtgtggaa gggaccaagc gaccaaggat aggccatctg | 1860 |
| gggtctatgc ccacataccc acgttttgttc gcttcctgag tcttttcatt gctacctcta | 1920 |
| atagtcctgt ctcccacttc ccactcgttc cctcctctt ccgagctgct ttgtgggctc | 1980 |
| aaggcctgta ctcatcggca ggtgcatgag tatctgtggg agtcctctag agagatgaga | 2040 |
| agccaggagg cctgcaccaa atgtcagaag cttggcatga cctcattccg ccacatcat | 2100 |
| tctgtgtctc tgcatccatt tgaacacatt attaagcact gataataggt agcctgctgt | 2160 |
| ggggtataca gcattgactc agatatagat cctgagctca cagagtttat agttaaaaaa | 2220 |
| acaaacagaa acacaaacaa tttggatcaa aaggagaaaa tgataagtga caaaagcagc | 2280 |
| acaaggaatt tccctgtgtg gatgctgagc tgtgatggca ggcactgggt acccaagtga | 2340 |
| aggttcccga ggacatgagt ctgtaggagc aagggcacaa actgcagctg tgagtgcgtg | 2400 |
| tgtgtgattt ggtgtaggta ggtctgtttg ccacttgatg gggcctgggt ttgttcctgg | 2460 |
| ggctggaatg ctgggtatgc tctgtgacaa ggctacgctg acaatcagtt aaacacaccg | 2520 |

-continued

```
gagaagaacc atttacatgc accttatatt tctgtgtaca catctattct caaagctaaa    2580
gggtatgaaa gtgcctgcct tgtttatagc cacttgtgag taaaaatttt tttgcatttt    2640
cacaaattat actttatata aggcattcca cacctaagaa ctagttttgg gaaatgtagc    2700
cctgggttta atgtcaaatc aaggcaaaag gaattaaata atgtactttt ggctaaaaaa    2760
aaaaaaaaaa aaaaaaaaaa aaaaaaaaaa aaaaaaaaaa aa                       2802
```

<210> SEQ ID NO 4
<211> LENGTH: 473
<212> TYPE: PRT
<213> ORGANISM: Artificial Sequence
<220> FEATURE:
<223> OTHER INFORMATION: Description of Artificial Sequence: [Deduced
      amino acid sequence of vitamin D receptor related gamma-2
      (VDRRg-2)]

<400> SEQUENCE: 4

```
Met Thr Val Thr Arg Thr His His Phe Lys Glu Gly Ser Leu Arg Ala
 1               5                  10                  15

Pro Ala Ile Pro Leu His Ser Ala Ala Ala Glu Leu Ala Ser Asn His
            20                  25                  30

Pro Arg Gly Pro Glu Ala Asn Leu Glu Val Arg Pro Lys Glu Ser Trp
        35                  40                  45

Asn His Ala Asp Phe Val His Cys Glu Asp Thr Glu Ser Val Pro Gly
    50                  55                  60

Lys Pro Ser Val Asn Ala Asp Glu Glu Val Gly Gly Pro Gln Ile Cys
65                  70                  75                  80

Arg Val Cys Gly Asp Lys Ala Thr Gly Tyr His Phe Asn Val Met Thr
                85                  90                  95

Cys Glu Gly Cys Lys Gly Phe Phe Arg Arg Ala Met Lys Arg Asn Ala
            100                 105                 110

Arg Leu Arg Cys Pro Phe Arg Lys Gly Ala Cys Glu Ile Thr Arg Lys
        115                 120                 125

Thr Arg Arg Gln Cys Gln Ala Cys Arg Leu Arg Lys Cys Leu Glu Ser
    130                 135                 140

Gly Met Lys Lys Glu Met Ile Met Ser Asp Glu Ala Val Glu Glu Arg
145                 150                 155                 160

Arg Ala Leu Ile Lys Arg Lys Ser Glu Arg Thr Gly Thr Gln Pro
                165                 170                 175

Leu Gly Val Gln Gly Leu Thr Glu Glu Gln Arg Met Met Ile Arg Glu
            180                 185                 190

Leu Met Asp Ala Gln Met Lys Thr Phe Asp Thr Thr Phe Ser His Phe
        195                 200                 205

Lys Asn Phe Arg Leu Pro Gly Val Leu Ser Ser Gly Cys Glu Leu Pro
    210                 215                 220

Glu Ser Leu Gln Ala Pro Ser Arg Glu Glu Ala Ala Lys Trp Ser Gln
225                 230                 235                 240

Val Arg Lys Asp Leu Cys Ser Leu Lys Val Ser Leu Gln Leu Arg Gly
                245                 250                 255

Glu Asp Gly Ser Val Trp Asn Tyr Lys Pro Pro Ala Asp Ser Gly Gly
            260                 265                 270

Lys Glu Ile Phe Ser Leu Leu Pro His Met Ala Asp Met Ser Thr Tyr
        275                 280                 285

Met Phe Lys Gly Ile Ile Ser Phe Ala Lys Val Ile Ser Tyr Phe Arg
    290                 295                 300
```

```
Asp Leu Pro Ile Glu Asp Gln Ile Ser Leu Leu Lys Gly Ala Ala Phe
305                 310                 315                 320

Glu Leu Cys Gln Leu Arg Phe Asn Thr Val Phe Asn Ala Glu Thr Gly
            325                 330                 335

Thr Trp Glu Cys Gly Arg Leu Ser Tyr Cys Leu Glu Asp Thr Ala Gly
            340                 345                 350

Gly Phe Gln Gln Leu Leu Leu Glu Pro Met Leu Lys Phe His Tyr Met
            355                 360                 365

Leu Lys Lys Leu Gln Leu His Glu Glu Glu Tyr Val Leu Met Gln Ala
            370                 375                 380

Ile Ser Leu Phe Ser Pro Asp Arg Pro Gly Val Leu Gln His Arg Val
385                 390                 395                 400

Val Asp Gln Leu Gln Glu Gln Phe Ala Ile Thr Leu Lys Ser Tyr Ile
            405                 410                 415

Glu Cys Asn Arg Pro Gln Pro Ala His Arg Phe Leu Phe Leu Lys Ile
            420                 425                 430

Met Ala Met Leu Thr Glu Leu Arg Ser Ile Asn Ala Gln His Thr Gln
            435                 440                 445

Arg Leu Leu Arg Ile Gln Asp Ile His Pro Phe Ala Thr Pro Leu Met
            450                 455                 460

Gln Glu Leu Phe Gly Ile Thr Gly Ser
465                 470
```